United States Patent
Saito et al.

(10) Patent No.: US 9,945,881 B2
(45) Date of Patent: Apr. 17, 2018

(54) AUTOMATIC ANALYSIS DEVICE (71) Applicant: HITACHI HIGH-TECHNOLOGIES CORPORATION, Tokyo (JP)

(72) Inventors: Yoshiaki Saito, Tokyo (JP); Toshihide Orihashi, Tokyo (JP); Kazuhiro Nakamura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/112,832

(22) PCT Filed: Jan. 16, 2015

(86) PCT No.: PCT/JP2015/051104
§ 371 (c)(1),
(2) Date: Jul. 20, 2016

(87) PCT Pub. No.: WO2015/115210
PCT Pub. Date: Aug. 6, 2015

(65) Prior Publication Data
US 2016/0341753 A1 Nov. 24, 2016

(30) Foreign Application Priority Data

Jan. 29, 2014 (JP) ................. 2014-014544

(51) Int. Cl.
*G01N 35/02* (2006.01)
*G01N 35/10* (2006.01)
(Continued)

(52) U.S. Cl.
CPC ............ *G01N 35/025* (2013.01); *B01L 3/021* (2013.01); *B01L 3/527* (2013.01); *B01L 99/00* (2013.01);
(Continued)

(58) Field of Classification Search
CPC .......... G01N 35/025; G01N 35/00722; G01N 35/1002; G01N 35/0092; G01N 35/10;
(Continued)

(56) References Cited

U.S. PATENT DOCUMENTS 4,641,674 A * 2/1987 Batjer ................... B04B 5/0407
134/138
5,783,450 A * 7/1998 Yoshida ................. G01N 30/88
422/70

(Continued)

FOREIGN PATENT DOCUMENTS

EP 0359049 A2 3/1990
EP 1 835 292 A1 9/2007

(Continued)

OTHER PUBLICATIONS

International Search Report of PCT/JP2015/051104 dated Apr. 14, 2015.
International Preliminary Report on Patentability received in corresponding International Application No. PCT/JP2015/051104 dated Aug. 11, 2016.

(Continued)

*Primary Examiner* — Sally A Merkling
(74) *Attorney, Agent, or Firm* — Mattingly & Malur, PC (57) ABSTRACT

After an analysis start instruction is input in a state where a sample is not dispensed to all of reaction containers 104 mounted on a reaction disc 105, before completing an analysis preparation washing process for washing the reaction container 104 to be used in analyzing the sample to be first analyzed, a soaking and washing process for performing soaking and washing during a predetermined period of time is controlled to be started by dispensing a soaking and washing detergent to another reaction container 104 different from the reaction container 104. In this manner, the soaking and washing can be efficiently performed on the reaction container without hindering an analysis process.

6 Claims, 8 Drawing Sheets

(51) Int. Cl.
*B01L 99/00* (2010.01)
*G01N 35/00* (2006.01)
*B01L 3/02* (2006.01)
*B01L 3/00* (2006.01)
*G01N 35/04* (2006.01)

(52) U.S. Cl.
CPC ... *G01N 35/0092* (2013.01); *G01N 35/00722* (2013.01); *G01N 35/10* (2013.01); *G01N 35/1002* (2013.01); *B01L 2200/147* (2013.01); *B01L 2300/0654* (2013.01); *B01L 2300/0841* (2013.01); *G01N 2035/00891* (2013.01); *G01N 2035/0437* (2013.01)

(58) Field of Classification Search
CPC .. G01N 2035/00891; G01N 2035/0437; B01L 3/021; B01L 3/527; B01L 99/00; B01L 2200/147; B01L 2300/0841; B01L 2300/0654
See application file for complete search history.

(56) References Cited

U.S. PATENT DOCUMENTS

| | | | |
|---|---|---|---|
| 6,500,388 B1* | 12/2002 | Nagaoka | G01N 35/02 134/169 R |
| 9,606,134 B2* | 3/2017 | Kanayama | G01N 35/025 |
| 2010/0108097 A1 | 5/2010 | Xueping et al. | |

FOREIGN PATENT DOCUMENTS

| | | |
|---|---|---|
| EP | 2 372 371 A2 | 10/2011 |
| JP | 63-033662 A | 2/1988 |
| JP | 02-080962 A | 3/1990 |
| JP | 05-018979 A | 1/1993 |
| JP | 2008-281454 A | 11/2008 |

OTHER PUBLICATIONS

Extended European Search Report received in corresponding European Application No. 15743224.6 dated Sep. 13, 2017.

* cited by examiner

| REACTION CONTAINER 902a — 902 — 901 | | | SAMPLE DISPENSING MECHANISM — 904 | |
|---|---|---|---|---|
| | ADDITIONAL WASHING | DATE OF PREVIOUS WASHING | DATE OF PREVIOUS WASHING | NUMBER OF TIMES |
| 1 | ☐ | 2013/07/10 | 2013/07/10 | 5 |
| 2 | ☐ | 2013/07/08 | | |
| 3 | ☐ | 2013/07/08 | REAGENT DISPENSING MECHANISM — 905 | |
| 4 | ☐ | 2013/07/05 | DATE OF PREVIOUS WASHING | NUMBER OF TIMES |
| 5 | ☐ | 2013/07/10 | 2013/07/10 | 1 |
| 6 | ☑ | 2013/07/09 | | |
| 7 | ☐ | 2013/07/08 | | |
| 8 | ☐ | 2013/07/05 | | |

CELL BLANK VALUE (REACTION CONTAINER: 6) — 903

| | 340 | 405 | 450 | 480 | 505 | 546 | 570 | 600 | 660 | 700 | 750 | 800 |
|---|---|---|---|---|---|---|---|---|---|---|---|---|
| 2013/07/10 | 12908 | 10865 | 10370 | 10215 | 9954 | 9800 | 9699 | 9524 | 9222 | 9180 | 8979 | 8865 |
| 2013/07/03 | 12961 | 10892 | 10395 | 10241 | 9978 | 9823 | 9711 | 9546 | 9241 | 9196 | 8993 | 8876 |
| 2013/06/26 | 12931 | 10878 | 10382 | 10228 | 9968 | 9811 | 9700 | 9536 | 9230 | 9187 | 8982 | 8866 |
| 2013/06/19 | 12941 | 10883 | 10389 | 10235 | 9974 | 9819 | 9709 | 9544 | 9237 | 9193 | 8992 | 8876 |
| 2013/06/12 | 12940 | 10883 | 10389 | 10238 | 9974 | 9819 | 9707 | 9542 | 9234 | 9190 | 8985 | 8870 |

AUTOMATIC ANALYSIS DEVICE

TECHNICAL FIELD

The present invention relates to an automatic analysis device which performs quantitative and qualitative analyses on a biological sample such as blood and urine.

BACKGROUND ART

An automatic analysis device has a washing mechanism and a washing tank which wash a reaction container for mixing a sample and a reagent or a probe used in dispensing by using water or a predetermined detergent, immediately before use. The automatic analysis device aims to prevent analysis accuracy from being degraded due to dirt adhering to the reaction container or the probe. However, blood or urine as an analysis target sample contains proteins and lipids. Thus, the automatic analysis device is in a situation where the dirt is likely to adhere to the reaction container or the probe. In addition, since the reaction container or the probe is repeatedly used, it is difficult to remove the adhering dirt by only performing washing immediately before.

Therefore, for example, the dirt adhering to the reaction container or the probe is removed by periodically performing maintenance in which the inside of the reaction container or the probe is soaked in a high concentration detergent for a fixed period of time. For example, PTL 1 (JP-A-2008-281454) discloses that the reaction container or the probe is soaked and washed by utilizing a period of time while a device is not used for analysis, such as during standby.

CITATION LIST

Patent Literature

PTL 1: JP-A-2008-281454

SUMMARY OF INVENTION

Technical Problem

Incidentally, in facilities in which an automatic analysis device is always operated for 24 hours in preparation for urgent sample arrival, even if soaking and washing are performed during standby as in the related art, in a case where an urgent sample analysis is needed, the soaking and washing have to be stopped, and there is no guarantee that a time for soaking can be sufficiently secured. In addition, if an operator tries to forcibly complete the soaking and washing, it is considered that an analysis process is hindered, thereby causing a possibility of degraded analysis efficiency.

The present invention is made in view of the above-described circumstances, and an object thereof is to provide an automatic analysis device which can efficiently perform soaking and washing on a reaction container without hindering an analysis process.

Solution to Problem

In order to achieve the above-described object, according to the invention, there is provided an automatic analysis device including a sample container conveyance path that conveys multiple sample containers containing a sample as an analysis target, a reagent disc on which multiple reagent containers containing a reagent for use in analyzing the sample are mounted, a reaction disc that arranges multiple reaction containers for mixed reaction between the sample and the reagent so as to be side by side in a circumferential direction, and that conveys the reaction container, a sample dispensing mechanism that dispenses the sample to the reaction container of the reaction disc from the sample container, a reagent dispensing mechanism that dispenses the reagent to the reaction container of the reaction disc from the reagent container of the reagent disc, and a control device that controls a soaking and washing process for performing soaking and washing during a predetermined period of time to be started by dispensing a soaking and washing detergent to another reaction container different from the reaction container, after an analysis start instruction is input in a state where the sample is not dispensed to all of the reaction containers mounted on the reaction disc, before completing an analysis preparation washing process for washing the reaction container to be used in analyzing the sample to be first analyzed.

Advantageous Effects of Invention

According to the present invention, soaking and washing can be efficiently performed on a reaction container without hindering an analysis process.

DESCRIPTION OF EMBODIMENTS

An embodiment of the invention will be described with reference to the drawings.

Figure 1:
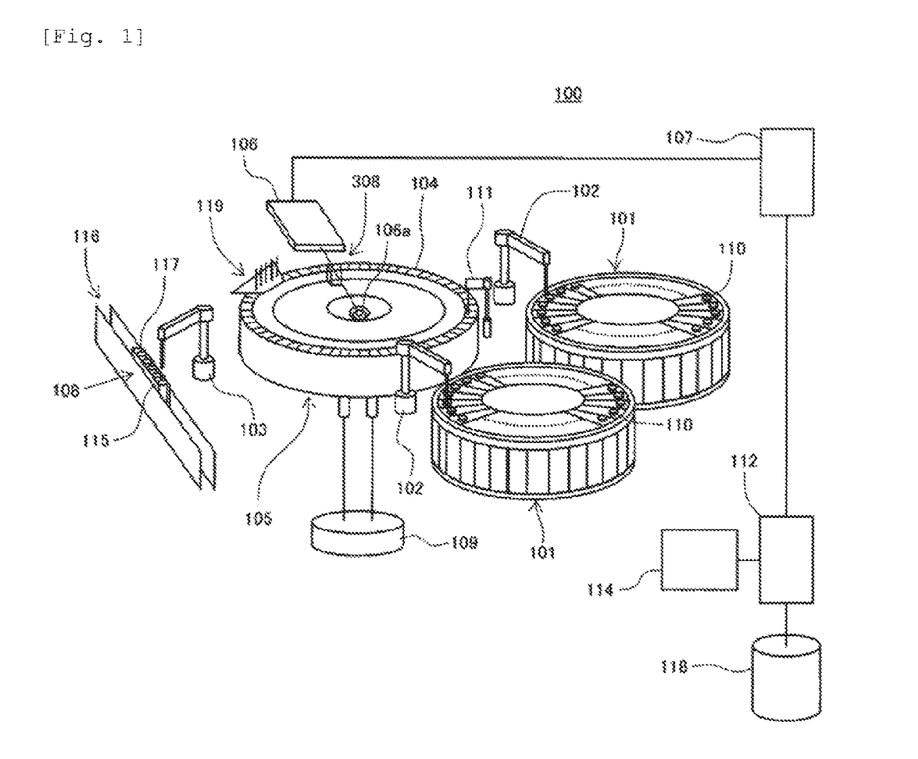
FIG. 1 is a view schematically illustrating a configuration of an automatic analysis device according to an embodiment of the invention.

FIG. 1 is a view schematically illustrating a configuration of an automatic analysis device according to the embodiment of the invention.

In FIG. 1, an automatic analysis device 100 schematically includes a sample container conveyance path 116 that conveys a sample container rack 115 on which a sample container 117 for containing a biological sample (hereinafter, simply referred to as a sample) such as blood and urine which are quantitative and qualitative analysis targets is mounted, a reagent disc 101 on which multiple reagent containers 110 for containing a reagent used in analyzing the sample are mounted, a reaction disc 105 that arranges multiple reaction containers 104 for mixed reaction between the sample and the reagent so as to be side by side in a circumferential direction, and that conveys the reaction container 104, a sample dispensing mechanism 103 that dispenses the sample to the reaction container 104 of the reaction disc 105 from the sample container 117 conveyed to a sample dispensing position 108 by the sample container conveyance path 116, a reagent dispensing mechanism 102 that dispenses the reagent to the reaction container 104 of the reaction disc 105 from the reagent container 110 of the reagent disc 101, and a control device 112 that controls an operation of a multi-wavelength photometer 106 for measuring light obtained from a light source 106a via the reaction container 104 and the overall automatic analysis device 100.

The sample container rack 115 having the sample container 117 mounted thereon is conveyed to the sample dispensing position 108 by the sample container conveyance path 116. The sample contained in the sample container 117 is subjected to suction by the sample dispensing mechanism 103. A predetermined amount of the sample is dispensed into the reaction container 104 arranged in the reaction disc 105.

The reaction container 104 to which the sample is discharged is moved to a reagent adding position by the reaction disc 105 whose temperature is controlled after communicating with a thermostatic tank 109. At this time, the reagent disc 101 performs a rotary operation so as to move the reagent container 110 corresponding to an analysis item to below the reagent dispensing mechanism 102. Then, a predetermined amount of the reagent subjected to suction from the reagent container 110 is dispensed to the reaction container 104 moved to the reagent adding position by the reagent dispensing mechanism 102. After the reagent is dispensed, the reaction container 104 is moved to a position of a mixing device 111 so as to perform initial mixing.

A light beam emitted from the light source 106a passes through the reaction container 104 in which the dispensed sample and reagent are mixed with each other, and is incident on the multi-wavelength photometer 106. In this manner, light absorbance of a reaction liquid which is content of the reaction container 104 is detected by the multi-wavelength photometer 106. A detected light absorbance signal is transmitted to the control device 112 via analog/digital (A/D) converter 107 and an interface (not illustrated). The light absorbance signal (that is, a measurement value) transmitted to the control device 112 is converted into analysis item concentration of a measurement target in the sample, is displayed on a display input unit 114 disposed in the control device 112, and is stored in a storage device 118 disposed in the control device 112.

The display input unit 114 is a graphic user interface (GUI) for displaying an analysis result or an operation screen. In a state where the operation screen is displayed, a button displayed on the operation screen is clicked by using a mouse pointer. In this manner, various operations and settings can be performed in the automatic analysis device 100.

The reaction container 104 in which the contained reaction liquid is completely measured is moved to a position of a washing mechanism 119. After a liquid (reaction liquid) contained therein is subjected to suction and washing (to be described in detail later), the reaction container 104 is provided for the subsequent analysis.

Figure 2:
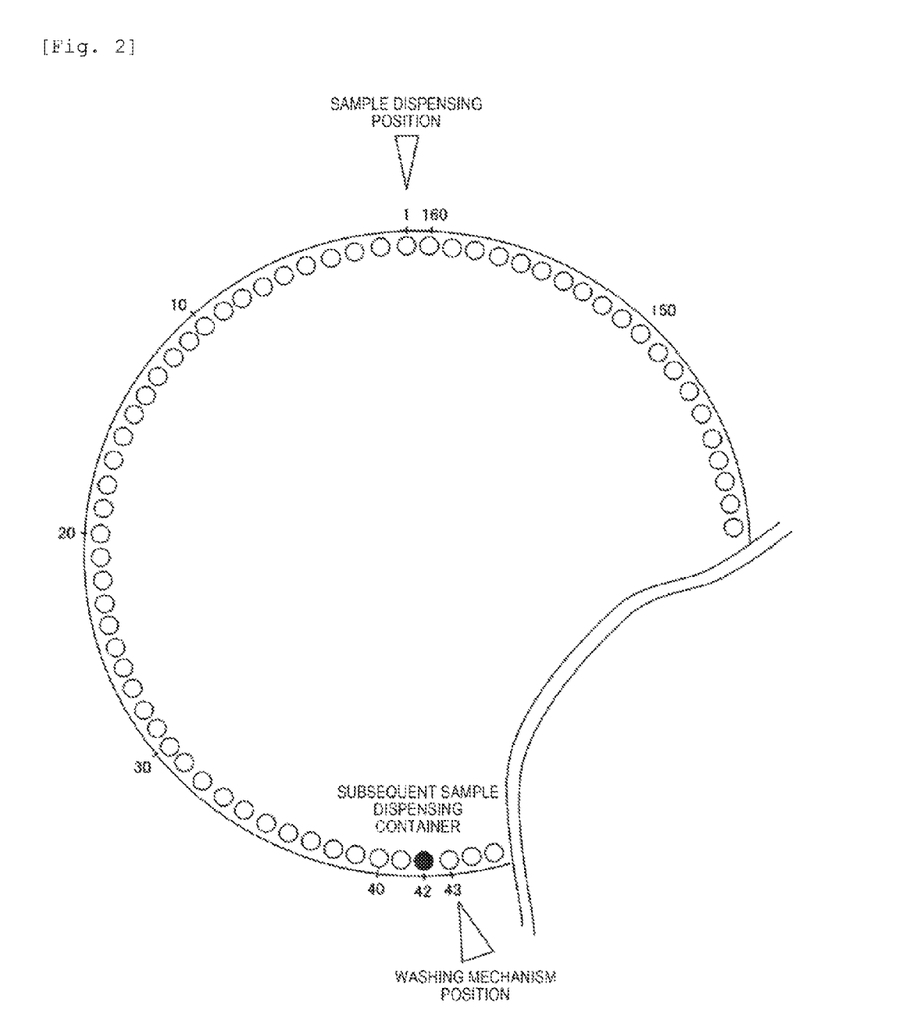
FIG. 2 is a view schematically illustrating an arrangement example of a reaction container on a reaction disc.

FIG. 2 is a view schematically illustrating an arrangement example of the reaction container on the reaction disc.

As illustrated in FIG. 2, the reaction containers 104 are arranged side by side in a circumferential direction on the reaction disc 105. The reaction disc 105 is periodically rotated at equal angles so as to move the reaction containers 104 to a predetermined circumferential position. While the reaction disc 105 is stopped, the reagent dispensing mechanism 102 and the sample dispensing mechanism 103 which perform a dispensing process, and the washing mechanism 119 which performs a washing process can have access to the reaction container 104. The respective mechanisms perform various processes on the reaction container 104 which stops at an operable position. That is, the respective mechanisms periodically and repeatedly perform an operation corresponding to each process on the periodically moving reaction container 104, thereby causing an analysis process to move forward.

For example, FIG. 2 illustrates a state where 160 reaction containers 104 are arranged side by side in the circumferential direction (rotation direction) of the reaction disc 105. For example, if it is assumed that the reaction disc 105 is rotated so as to move a distance corresponding to 41 reaction containers while the reaction container 104 mounted on the reaction disc 105 is moved one round (hereinafter, referred to as a cycle), in a cycle subsequent to the cycle in which the sample dispensing process is performed on the reaction container 104 of No. 1, the sample dispensing operation is performed on the reaction container 104 of No. 42. In addition, if the reaction container 104 is moved on 160 cycles which are the same as the total number of the reaction containers 104 mounted on the reaction disc 105, the reaction container 104 of No. 1 returns again to the position for performing the sample dispensing process. That is, this process is similarly applied to the washing process performed by the washing mechanism 119. In a case where the washing process is first performed on the reaction container 104 of No. 43, the washing process is performed on the reaction container 104 of No. 84 on the subsequent cycle. After 160 cycles, the washing process is performed again on the reaction container 104 of No. 43. This process is also applied to other processes.

Figure 3:
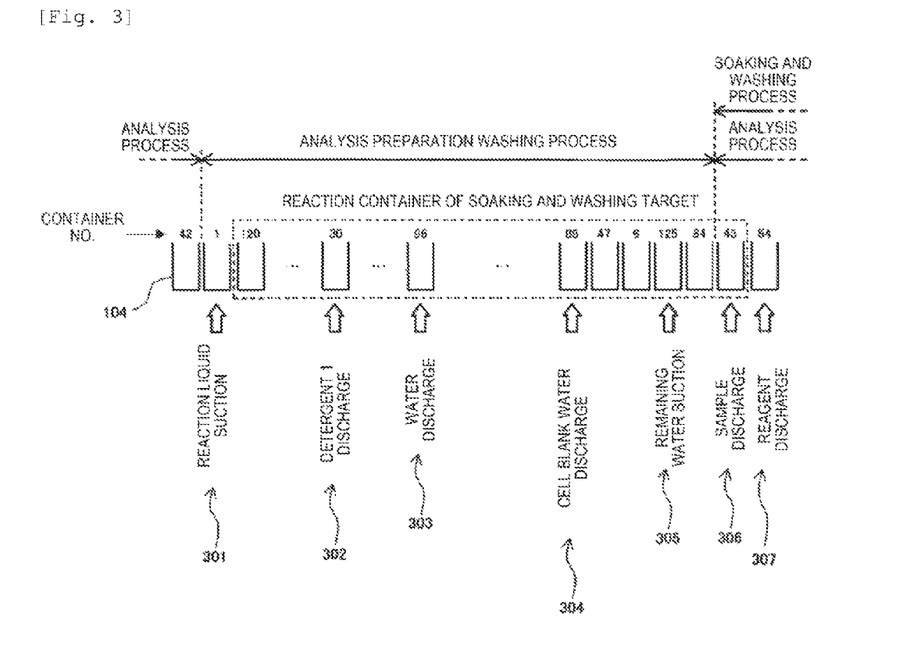
FIG. 3 is a view illustrating an example of a washing process performed by a washing mechanism before an analysis of the reaction container.

FIG. 3 is a view illustrating an example of the washing process performed by the washing mechanism before an analysis of the reaction container.

As illustrated in FIG. 3, the washing process before the analysis of the reaction container 104 (analysis preparation washing process) is configured to include multiple sub-processes. That is, the analysis preparation washing process is configured to include the multiple sub-processes such as a reaction liquid suction process, a detergent 1 discharge process, a water discharge process, a cell blank water discharge process, remaining water suction process, and multiple standby processes. Then, while the reaction disc 105 is stopped within one cycle, the washing mechanism 119 concurrently performs the process on the reaction containers 104 arriving at a reaction liquid suction position 301, a detergent 1 discharge position 302, a water discharge position 303, a cell blank water discharge position 304, and a remaining water suction position 305.

The reaction liquid suction process is a sub-process of performing a water discharge process at the reaction liquid suction position 301 by performing suction on the reaction liquid used for the previous analysis and discarding the reaction liquid as a waste liquid. For example, even in a case where those other than the reaction liquid such as water are contained in the reaction container 104, the water is similarly subjected to suction, and is discarded as the waste liquid. In this manner, the process of discharging the water is performed.

The detergent 1 discharge process is a sub-process of discharging a detergent 1 by performing suction on the water discharged in the reaction liquid suction process at the detergent 1 discharge position 302.

The water discharge process is a sub-process of discharging rinsing water by performing suction on the detergent 1 discharged in the detergent 1 discharge process at the water discharge position 303.

The cell blank water discharge process is a sub-process of discharging water at the cell blank water discharge position 304 in order to measure a cell blank value.

The remaining water suction process is a sub-process of performing suction on all water inside the reaction container 104 at the remaining water suction position 305 so as to remove remaining water for the subsequent analysis.

The standby process is a sub-process of standing by without performing any special process on the reaction container 104 during a period between the respective sub-processes.

In FIG. 3, the right side process in each process represents the subsequent process, and indicates that the process moves forward as each reaction container 104 moves to the right side. That is, each time the reaction disc 105 is rotated as much as a regulated angle on each cycle (that is, each time one cycle moves forward), the reaction container 104 subjected to washing at the respective positions 301 to 305 included in the washing mechanism 119 is located at a position of the reaction container 104 which is shifted one to the right in FIG. 3. For example, on a cycle subsequent to the process in which the remaining water suction process is performed on the reaction container 104 of container No. 125 in FIG. 3, the reaction container 104 of No. 6 arrives at the remaining water suction position 305, thereby performing the remaining water suction process.

Then, the respective reaction containers 104 can be used for the analysis after a series of analysis preparation washing processes is performed in the order of at least the reaction liquid suction process, the detergent 1 discharge process, the water discharge process, the cell blank water discharge process, and the remaining water suction process.

For example, in a case where setting is made so that the reaction container 104 of No. 1 is first used for an analysis process, if an analysis start instruction is input by an operator pressing down a start button, the reaction container 104 of No. 1 is first moved to the reaction liquid suction position 301 in order to start the analysis after the washing process is first performed on the reaction container 104 of No. 1. Since the previous analysis process is completed, when the analysis start instruction is input, the sample is in a state where the sample is not dispensed to all of the reaction containers 104 mounted on the reaction disc 105. Except for a special case, in this state, the analysis start instruction is input. Thereafter, the reaction liquid suction process is performed on the reaction container of No. 1 so as to start periodical control for the reaction disc 105. While the reaction container of No. 1 arrives at the sample discharge position 306 from when the washing starts, since the reaction container which can be analyzed is not present, the sample is caused to stand by for the sample dispensing. Hereinafter, a washing period after the washing process starts for the reaction container 104 of No. 1 before one cycle on which the reaction container 104 of No. 1 arrives at the sample discharge position 306 and the sample is dispensed is referred to as the analysis preparation washing process. In some cases, the reagent is dispensed earlier than the sample. Accordingly, in this case, during the washing period before one cycle on which the reagent is dispensed, the analysis preparation washing process is performed. In this example, a case is described where 38 cycles are needed to completely perform the analysis preparation washing process on the reaction container 104. The number of cycles for the analysis preparation washing process is uniquely determined depending on the number of the reaction containers of the automatic analysis device 100, the sample dispensing mechanism 103 and the reaction liquid suction position 301 of the washing mechanism 119, and the number of the reaction containers operated on one cycle.

In addition, as partially illustrated in FIG. 3, an analyzing process (analysis process) for the sample is also configured to include multiple sub-processes. That is, the analysis process is configured to include the multiple sub-processes such as a sample discharge process, a reagent discharge process, and a measurement process (not illustrated).

The sample discharge process is a sub-process of discharging an analysis target sample to the reaction container 104 which completes the analysis preparation washing process, at the sample discharge position 306.

The reagent discharge process is a sub-process of discharging the reagent to the reaction container 104 from which the sample is discharged in the sample discharge process, at the reagent discharge position 307. In a case where the reagent is discharged earlier, the sample discharge process is a sub-process of discharging the sample to the reaction container 104 from which the reagent is discharged.

The measurement process is a sub-process of measuring light absorbance of the reaction liquid when the reaction container 104 containing the reaction liquid in which the sample and the reagent are mixed with each other passes through a measurement position 308 (refer to FIG. 1) (or stops at the measurement position 308). Therefore, it is not always necessary to perform the measurement process while the reaction disc 105 is stopped.

Next, the soaking and washing will be described. In the analysis process, the reaction container 104 which completes all of the predetermined analysis preparation washing processes starting from the reaction liquid suction process, that is, the reaction container 104 for which washing is guaranteed in the analysis preparation washing process is allowed to start the analysis process. Therefore, when the analysis preparation washing process starts, the reaction container 104 (reaction container of No. 120 in FIG. 3) located at a position where one cycle moves forward from the reaction liquid suction position arrives at the sample discharge position earlier than the reaction container 104 (reaction container of No. 1 in FIG. 3) located at the reaction liquid suction position at the same time. However, the analysis process does not start. According to the present embodiment, in parallel with the analysis preparation washing which causes the sample dispensing to stand by, the soaking and washing are performed on the reaction container 104 arriving at the sample discharge position 306 earlier than the reaction container 104 for which the analysis process is first started. The soaking and washing are performed on the reaction container 104 arriving at the sample discharge position 306 in such a way that a soaking and washing detergent is discharged to the reaction container 104 by the sample dispensing mechanism 103. In addition, in a case where a dispensing amount of the sample dispensing mechanism 103 is not sufficient in discharging the soaking and washing detergent, the reagent dispensing mechanism 102 may be configured to discharge the soaking and washing detergent. Alternatively, a configuration may be adopted in which other multiple dispensing mechanisms are prepared so as to discharge the soaking and washing detergent to the reaction container 104.

In the example illustrated in FIG. 3, the analysis preparation washing process starts. In parallel to the washing process performed by the washing mechanism 119 in the order of the reaction container 104 of No. 1 and the reaction container 104 of No. 42, the soaking and washing detergent is discharged to the reaction container 104 of No. 43 in the order of the reaction container 104 of No. 84 by the sample dispensing mechanism 103 (and the reagent dispensing mechanism 102). After the number of processes (38 cycles) required for completing the analysis preparation washing process according to the present embodiment, on a cycle subsequent to the cycle where the soaking and washing detergent is completely discharged to the reaction container 104 of No. 120, the reacn container 104 of No. 1 for which the analysis preparation washing process is completely performed by the washing mechanism 119 arrives at the sample discharge position 306, thereby dispensing the sample.

In this way, during the analysis preparation washing on cycles, 38 reaction containers arrive at the sample discharge position 306. Accordingly, the soaking and washing can be performed on the 38 reaction containers 104. That is, the reaction container 104 filled with the soaking and washing detergent is subjected to the soaking and washing within a period until the reaction container 104 arrives at the reaction liquid suction position 301. As in this example, according to the analysis device including 160 reaction containers 104 so as to perform the analysis preparation washing on 38 cycles, the reaction containers 104 can be soaked during 122 cycles. The washing process is performed on the reaction container 104 subjected to the soaking and washing by the washing mechanism 119, and the reaction container 104 is used for the analysis process.

In other words, according to the present embodiment, in a case where an operator inputs the analysis start (return from a stopped state, or analysis start due to the return from a standby state) instruction, that is, in a state where the sample is not dispensed to all of the reaction containers 104 mounted on the reaction disc 105, the control device 112 is configured to include the analysis preparation washing process of washing the reaction containers 104 immediately before the reaction containers 104 is used for the analysis process, and the multiple sub-processes provided so as to partially overlap the analysis process, and includes a leading sub-process of dispensing the soaking and washing detergent to the reaction container 104. The control device 112 controls the soaking and washing process of performing the soaking and washing during a predetermined period of time by dispensing the soaking and washing detergent to the reaction container 104 so that all of these processes concurrently start.

In other words, after the analysis start instruction is input in a state where the sample is not dispensed to all of the reaction containers 104 mounted on the reaction disc, before the analysis preparation washing process of washing the reaction container to be used in analyzing the sample to be first analyzed is completely performed, the control device 112 controls the soaking and washing process for performing the soaking and washing during a predetermined period of time to be started by dispensing the soaking and washing detergent to another reaction container different from the reaction container.

According to this control, the soaking and washing detergent in the soaking and washing process is discharged to the reaction container 104 on which the analysis preparation washing process is first performed, while the minimum number of cycles required for completing the washing process move forward. Therefore, the soaking and washing can be performed on some of the reaction containers 104 without a need to provide a time for new soaking and washing which is required due to the increased number of cycles.

However, according to the invention, it is not always necessary to concurrently start the analysis preparation washing process of the reaction container 104 which is first subjected to the analysis preparation washing and the soaking and washing process of the reaction container 104 which is first subjected to the soaking and washing. In a case of the above-described example, an example has been described in which the soaking and washing are performed on 38 reaction containers 104. However, the start of the soaking and washing process of the reaction container 104 which is first subjected to the soaking and washing may be delayed as much as one cycle than the start of the analysis preparation washing process of the reaction container 104 which is first subjected to the analysis preparation washing. Even in this case, the soaking and washing can be performed on 37 reaction containers 104. However, in viewpoint of performing the soaking and washing on the reaction containers 104 as much as possible, it is desirable to concurrently start these processes for the reaction container 104 which is first subjected to the washing.

In addition, in the above-described example, the soaking and washing detergent is discharged by the sample dispensing mechanism 103 or the reagent dispensing mechanism 102. However, the invention is not limited thereto. A new dispensing mechanism for discharging a dischargeable soaking and washing detergent may be disposed at a position where the reaction container 104 passing through the dispensing position in the dispensing mechanisms arrives. In this case, although the new dispensing mechanism is added and the soaking time is shortened, the invention is applicable to this method. In this case, the number of cycles increases until the reaction container 104 for which the analysis preparation washing process is first started arrives at the dispensing position of the dedicated dispensing mechanism. Accordingly, the soaking and washing detergent can be dispensed to the reaction containers 104 as much as possible without affecting the analysis process start. However, it is desirable to adopt the above-described example in a viewpoint that the new dispensing mechanism is not needed and the longer soaking time is ensured.

According to the above-described example, before the analysis preparation washing process of the reaction container to be used in analyzing the sample to be first analyzed is completely performed, the sample dispensing mechanism 103 continues to dispense the soaking and washing detergent. After the analysis preparation washing process is completely performed, the sample dispensing mechanism 103 continues to dispense the sample for analysis. In addition, in a case where the soaking and washing detergent is dispensed by the reagent dispensing mechanism 102, similarly to a case where the sample is replaced with the reagent, before the analysis preparation washing process is completely performed, the reagent dispensing mechanism. 102 continues to dispense the soaking and washing detergent. After the process is completely performed, the reagent dispensing mechanism 102 continues to dispense the reagent for analysis.

In a single soaking and washing process, the number of the reaction containers 104 which can be subjected to the soaking and washing depends on a cycle of the analysis preparation washing process. In the present embodiment, the multiple reaction containers 104 mounted on the reaction disc 105 are divided into a block (reaction container group) configured to include the number of the reaction containers 104 which can be subjected to the soaking and washing once. The soaking and washing are performed on each block. For example, in a case where the number of the reaction containers 104 which can be subjected to soaking once is 38 within 160 reaction containers in total, the reaction containers can be divided into at least 5 blocks.

That is, in a case where the total number of the reaction containers is set to N (N is a natural number) and the number of the reaction containers subjected to the soaking and washing is set to M (M is a natural number), the reaction containers can be divided into the number of blocks corresponding to the quotient of N/M. In addition, the number of cycles applied to the analysis preparation washing process corresponds to the maximum number of the reaction containers subjected to the soaking and washing. Accordingly, if the number of cycles is set to L (M≤L) (L is a natural number), the number corresponding to the quotient of N/L represents the minimum number of blocks.

Figure 4:
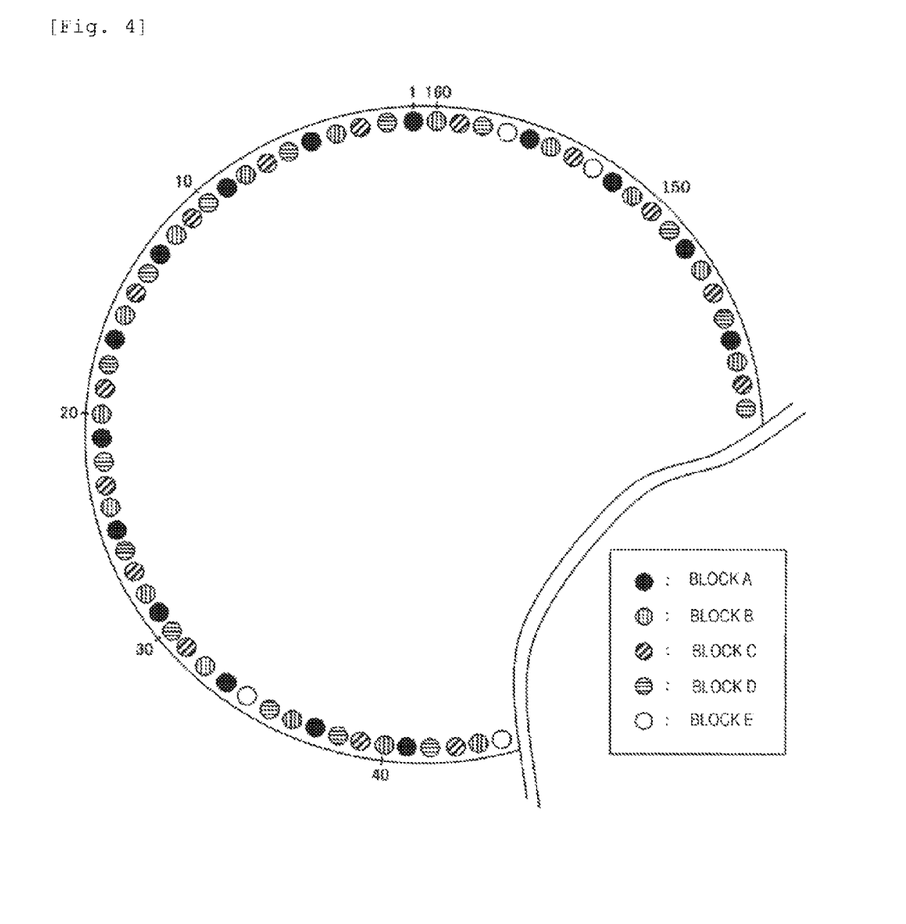
FIG. 4 is a view illustrating an example of block division of the reaction containers.

FIG. 4 is a view illustrating an example of block division of the reaction containers.

FIG. 4 illustrates a case where the multiple reaction containers 104 arranged on the reaction disc 105 are divided into Block A to Block D as the reaction container group configured to include 38 reaction containers 104, and divided into Block E as the reaction container group configured to include 8 reaction containers 104.

For example, Block A is obtained by defining the total 38 reaction containers as one reaction container group in the order of using the reaction containers 104 which are determined by the rotation of the reaction disc, starting from the reaction container of No. 1 as a leading reaction container 104. In addition, similarly, Block B is obtained by defining the total 38 reaction containers as one reaction container group in the order of using the reaction containers 104 starting from the reaction container of No. 119 to be used the $39^{th}$ time as a leading reaction container 104. This is similarly applied to Block C, Block D, and Block E.

The reaction container 104 of No. 1 when a certain analysis starts, and the reaction containers 104 of No. 119, No. 77, No. 35, and No. 153 when the subsequent analysis starts are respectively controlled so as to move to the sample discharge position 306 before the analysis preparation washing starts. In this manner, the soaking and washing can be sequentially performed on all of the reaction containers 104.

That is, in order to perform the soaking and washing on all of the reaction containers 104, another block different from the block subjected to the previous soaking and washing may be washed whenever the analysis starts. Specifically, the leading reaction container 104 of the block for performing the soaking and washing may be moved to the sample discharge position 306. For example, in a case where the soaking and washing are previously performed on the reaction containers from No. 43 to No. 120, when the subsequent analysis starts, the analysis preparation washing may be performed after the reaction container of No. 1 is moved to the sample discharge position 306. The reaction disc 105 is controlled in this way. In this manner, for example, in a case of an operation in which the soaking and washing process starts when the analysis starts once every day, the soaking and washing can be performed on every one block a day. In this case, all of the blocks can be completely washed within 5 days, and the soaking and washing are performed again on the first block from the $6^{th}$ day. In this way, the soaking and washing can be performed on the reaction containers on a cycle of 5 days. Therefore, it is not necessary to individually spend the time for periodical maintenance.

The reaction container 104 belonging to one block may not be fixed. For example, in the example in FIG. 4, 8 reaction containers 104 are present in Block E. Accordingly, a configuration may be adopted in which 30 reaction containers 104 from the leading reaction container of Block A may be washed in accordance with the washing of Block E. This case has the same configuration as a case where the date and time of the previous washing are stored for each reaction container 104, and where a new block is configured to include the block having 38 reaction containers from the reaction container having the oldest date and time of the previous washing within all of the reaction containers.

In addition, the number of reaction containers in one block and the number of blocks may not be fixed. For example, an analysis device including 160 reaction containers 104 may be configured to include 5 blocks having 32 reaction containers 104 per block. In addition, as another example, the analysis device may have 6 blocks, and each block may be configured to include 26 or 27 reaction containers 104. It is desirable that the number of reaction containers 104 belonging to each block falls within the number of cycles of the analysis preparation washing (38 cycles in the present embodiment). The reason is that the soaking and washing can be performed without providing a time for new soaking and washing which are needed due to the increased number of cycles.

In addition, a case is also considered where the soaking and washing process is not limited to the process performed when the analysis starts from standby. For example, in a case of completing the analysis relating to all of the samples conveyed to the analysis device, the analysis device is in a standby state until a new sample is conveyed. Accordingly, it is also considered that the soaking and washing are performed on the reaction container immediately after the analysis device is brought into the standby state.

However, in a case where the automatic analysis device is not normally stopped, there is a possibility that the reaction liquid may remain in some reaction containers 104 of the washing target reaction container group. Therefore, in this case, for example, the storage device 118 may store information indicating whether or not the reaction liquid remains in all of the reaction containers 104, and may control the soaking and washing to be performed if there is no reaction container in which the reaction liquid remains in the soaking and washing target reaction container group. In addition, in a case where the reaction container 104 in which the remaining liquid is finally subjected to suction is contained in the soaking and washing target reaction container group, there is a possibility that the reaction liquid may remain in the soaking and washing target reaction container group. Accordingly, the soaking and washing are not performed at that time. In addition, in a case where the detergent is insufficient, similarly, the soaking and washing are not performed. In these cases, the soaking and washing are performed when the subsequent analysis starts. Alternatively, in a case where there is the remaining liquid in the soaking and washing target reaction container group, the remaining liquid may be discarded after the analysis starts. Thereafter, the soaking and washing may be performed without using the corresponding reaction container 104 for the analysis.

In addition, in a case where the detergent is insufficient, the analysis may start after the device is necessarily provided with the sufficient detergent by warning a user to add the detergent thereto.

Figure 5:
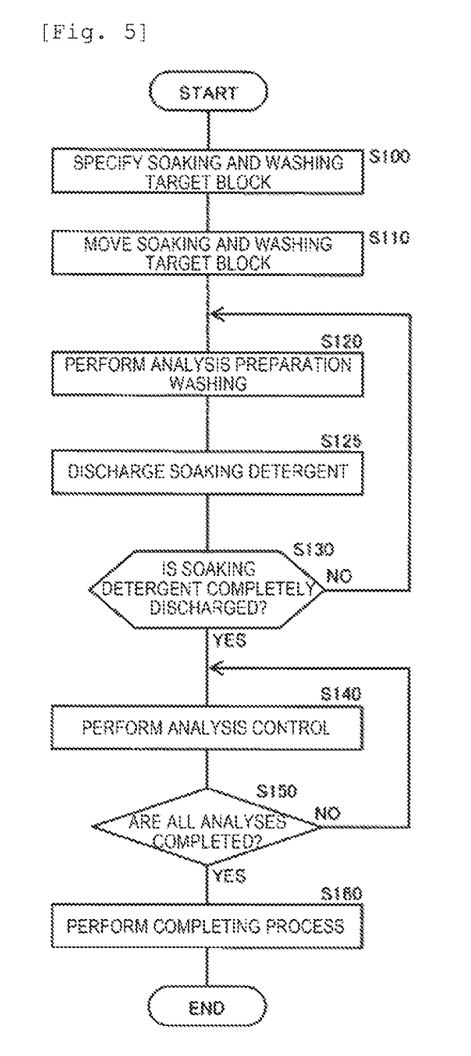
FIG. 5 is a flowchart illustrating a soaking and washing process.
Figure 6:
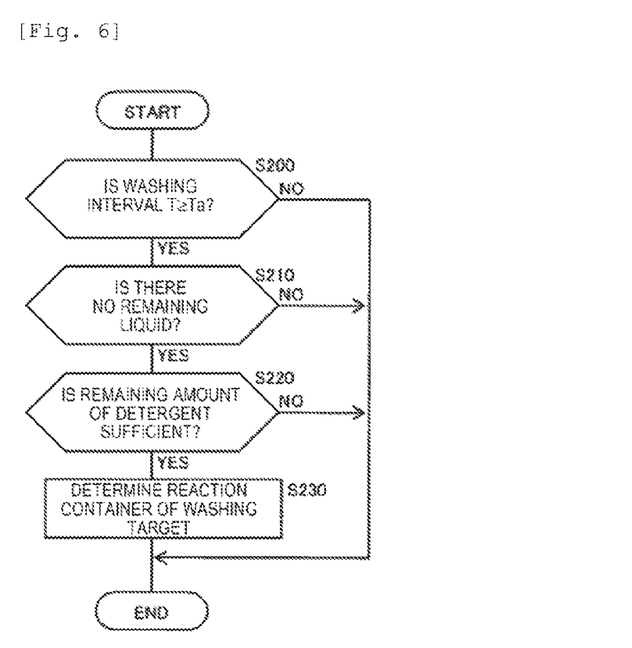
FIG. 6 is a flowchart illustrating a process of specifying a soaking and washing target block.

FIG. 5 is a flowchart illustrating the soaking and washing process. FIG. 6 is a flowchart illustrating a process of specifying a soaking and washing target block.

If an operator inputs an analysis start instruction, the control device 112 first performs the process of specifying the soaking and washing target blocks (to be described later) (Step S100).

Next, within the soaking and washing target blocks specified in Step S100, the reaction container 104 whose use order is earliest is moved to the sample discharge position 306 (Step S110). For example, in a case where Block B in FIG. 4 is the target block, the reaction container 104 whose use order is earliest within the determined block is the reaction container 104 of No. 119, and becomes a soaking and washing target container. If the time from the analysis start instruction until when the process (to be described later) starts is short, the analysis process starts early. Accordingly, the movement operation in Step S110 is a movement independent of the rotation stopping operation on one cycle of the reaction disc in the analysis preparation washing process. That is, in this case, the reaction container 104 of No. 119 is efficiently moved to the sample discharge position 306 without stopping at a position other than the sample discharge position 306.

Next, the analysis preparation washing process and a soaking detergent discharge process are concurrently performed (Steps S120 and S125). The rotation stopping operation of the reaction disc is repeatedly performed on every one cycle, thereby performing the processes. It is determined whether or not the soaking detergent is completely discharged to all of the reaction containers 104 in the soaking and washing target block (Step S130). In a case where the determination result is NO in Step S130, the processes in Steps S120 and S125 are repeatedly performed until the soaking detergent is completely discharged to all of the reaction containers 104 in the soaking and washing target block.

In addition, in a case where the determination result is YES in Step S130, the analysis control is performed (Step S140). In the analysis control, in accordance with requested analysis items, the sample is dispensed to the reaction container 104 arriving at the sample discharge position 306, and the reagent is dispensed to the reaction container 104 arriving at the reagent discharge position 307. Since the used reaction container 104 is washed and reused, the washing mechanism 119 continuously performs the washing process even during the analysis control.

Next, it is determined whether or not the analysis request is all completed (Step S150). In a case where the determination result is NO, the process in Step S140 is repeatedly performed until the determination result shows YES.

In addition, in a case where the determination result is YES in Step S150, all of the reaction containers are washed in order to bring all of the reaction containers into a state where the sample is not dispensed. A completing process is performed (Step S160), thereby completing the process by stopping the overall control.

In addition, in a case where a new analysis start instruction is input, the processes are performed in accordance with the flow from Step S100 of specifying the soaking and washing target block. That is, after the new analysis start instruction is input, the control device 112 conveys one reaction container in the reaction container group which is not the target for performing the previous soaking and washing process, to the position for dispensing the soaking and washing detergent, thereby starting the soaking and washing process. In addition, at this time, the reaction container is conveyed independently of the rotation stopping operation on one cycle of the reaction disc in the analysis preparation washing process.

In this way, the above-described control is repeatedly performed with the analysis start as a trigger. Accordingly, if attention is paid to one reaction container, while the soaking and washing process is performed twice, the reaction container is brought into either a state where the soaking and washing are completely performed on all of the reaction containers mounted on the reaction disc or a state where the soaking and washing process starts. Therefore, the soaking and washing can be equally performed on all of the reaction containers.

For the reaction container 104 subjected to the soaking and washing, a cell blank value functioning as a reference value may be subsequently measured, and the measured cell blank value may be stored in the storage device 118 of the device. In addition, each dispensing mechanism may be washed in accordance with the soaking and washing of the reaction container. Each probe can be sufficiently washed within a time shorter than the soaking and washing time of the reaction container. Accordingly, if the maximum number of soaking available reaction containers is set to Na, the number of the reaction containers in the washing target block is set to Nb, and the number of washing times for the dispensing mechanism is set to Nc, the washing can be performed in a case of Na≥Nb+Nc. The maximum number of soaking available reaction containers represents the number of reaction containers which can be subjected to the soaking and washing by single analysis start, and is 38 in the example in FIG. 2. In a case where the reaction containers are divided into blocks as illustrated in FIG. 4, the dispensing mechanism can also be washed in accordance with the soaking and washing of Block E.

As illustrated in FIG. 6, in the process of specifying the soaking and washing target block, the control device 112 performs a mechanism resetting operation, and thereafter, determines whether or not a preset fixed period of time Ta elapses at a washing interval T (Step S200). In a case where the determination result is NO, the control device 112 determines that there is no block in which the fixed period of time elapses and the soaking and washing are not needed, thereby completing the process.

In a case where the determination result is YES in Step S200, the control device 112 determines that there is a block in which the fixed period of time elapses, and determines whether or not the remaining liquid is absent in the block subjected to the soaking and washing in the most past within the target blocks (Step S210). In a case where the determination result is NO in Step S210, the control device 112 determines that the soaking and washing cannot be performed, thereby completing the process.

In a case where the determination result is YES in Step S210, the control device 112 determines whether or not the amount of the soaking detergent is sufficient (Step S220). In a case where the determination result is NO, the control device 112 determines that the soaking and washing cannot be performed, thereby completing the process.

In a case where the determination result is YES in Step S220, the control device 112 determines that the reaction container 104 whose use order is earliest in the block determined in Step S200 is the reaction container 104 to be moved to the sample discharge position 306 as the soaking and washing target container.

The determination in Step S200 is not limited to the date and time of the previous washing. For example, a method may be employed in which the number of dispensing times of the reagent containing a predetermined component is stored so that the block including the reaction container where the number of dispensing times is equal to or greater than a predetermined number of times is selected as a washing target.

Figure 7:
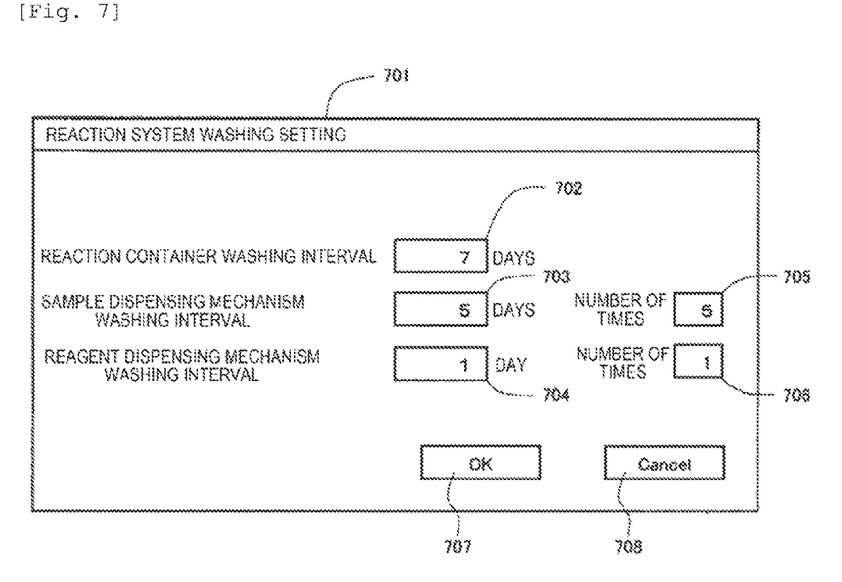
FIG. 7 is a view illustrating an example of a screen for setting a washing interval of the reaction container and each probe.

FIG. 7 is a view illustrating an example of a screen for setting a washing interval of the reaction container and each probe.

In FIG. 7, a reaction system washing setting screen 701 includes a washing interval input area 702 which sets an interval for performing the soaking and washing of the reaction container 104. In addition, the reaction system washing setting screen 701 includes washing interval input areas 703 and 704 which respectively set each washing interval of the sample dispensing mechanism 103 and the reagent dispensing mechanism 102, washing number input areas 705 and 706 which respectively set each number of washing times, an OK button 707 which determines an input setting value, and a cancellation button 708 which cancels the input setting value. In the example in FIG. 7, a unit of the washing interval of the reaction container is a day. However, the unit may be the number of use times of each reaction container 104 or the number of rounds. Here, for example, the number of rounds is a value obtained in such a way that a cycle on which the reaction container 104 of No. 1 arrives at the sample dispensing position and subsequently arrives at the sample dispensing position after the sample is dispensed is counted as one round. In a case where the unit is set using the number of use times or the number of rounds, the soaking and washing can be provided in accordance with a frequency of using the device for every facility.

Figure 8:
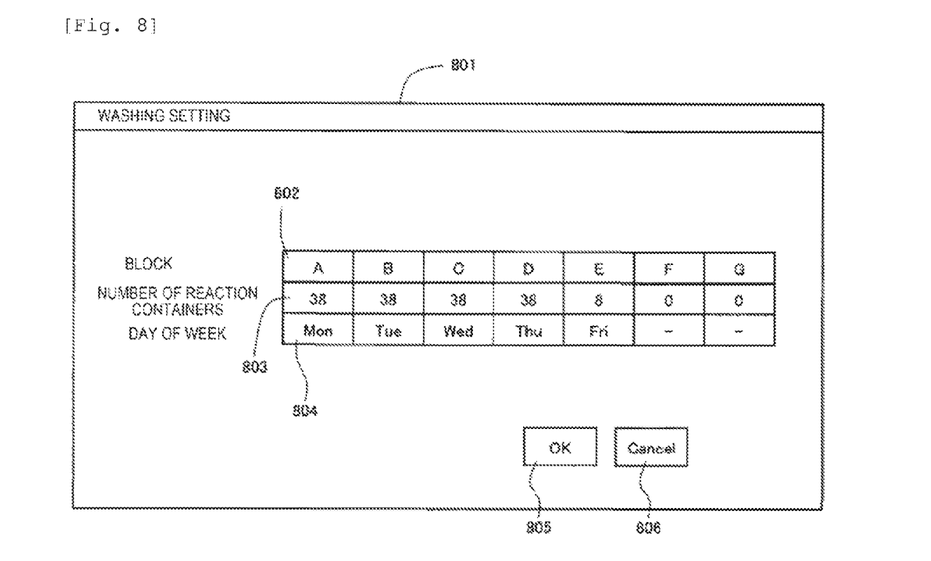
FIG. 8 is a view illustrating another example of a screen for setting a washing interval of the reaction container.

FIG. 8 is a view illustrating another example of a screen for setting a washing interval of the reaction container.

In FIG. 8, a washing setting screen 801 includes a block area 802 which displays a block name, a container number input area 803 which inputs the number of soaking and washing target reaction containers in each block, a day-of-week input area 804 which inputs the day of week for performing the soaking and washing on each block, an OK button 805 which determines an input setting value, and a cancellation button 806 which cancels the input setting value. The washing setting screen 801 represents a case where the soaking and washing interval of the reaction container 104 is set to one week. For example, in a case where the reaction containers are divided into blocks as illustrated in FIG. 4, and in a case where the soaking and washing are performed one block by one block on every day of week, the number of soaking and washing target containers and the day of week for performing the soaking and washing may be input to Block A to Block E as illustrated in FIG. 8.

Figure 9:
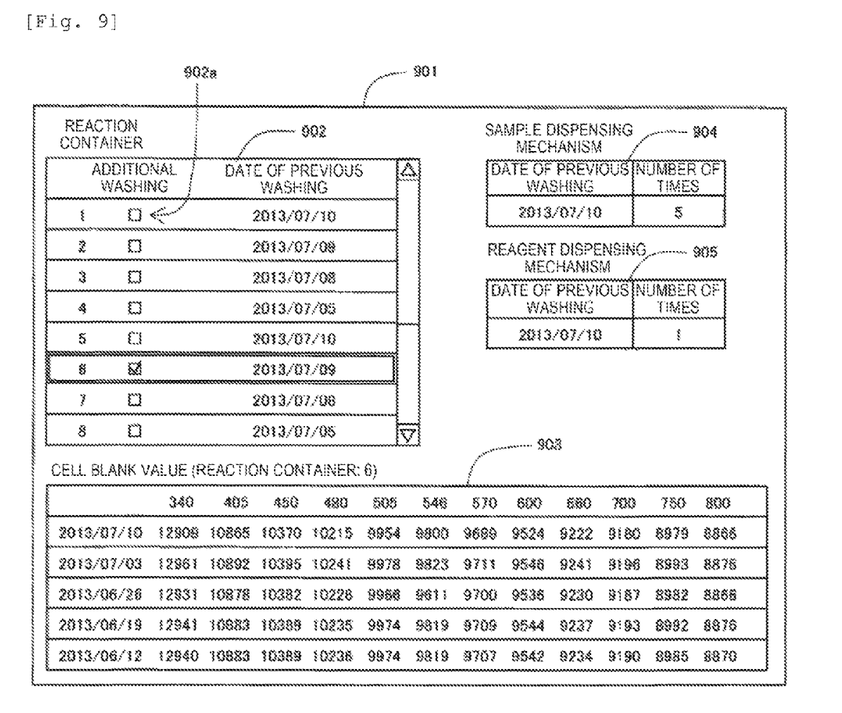
FIG. 9 is a view illustrating an example of a washing state display screen for displaying a washing state of the reaction container and each probe.

FIG. 9 is a view illustrating an example of a washing state display screen for displaying a washing state of the reaction container and each probe.

In FIG. 9, a washing state display screen 901 has a washing state display area 902 which displays a washing state of each reaction container, a cell blank value display area 903 which displays a cell blank value of the reaction container (for example, the reaction container of No. 6) selected by the washing state display area 902, a washing state display area 904 which displays a washing state of the sample dispensing mechanism 103, and a washing state display area 905 which displays a washing state of the reagent dispensing mechanism 102.

The washing state display area 902 displays a number of each reaction container 106 and the date when the previous soaking and washing are performed. In a case where a unit of the washing interval of the reaction container 104 is set to the number of use times or the number of rounds, the number of use times or the number of rounds from when the previous washing is performed may be displayed.

The cell blank value display area 903 displays the reaction container 106 selected by the washing state display area 902 in such a way that the date when the soaking and washing are performed and the cell blank value is measured and the cell blank value of each wavelength are retroactively applied to several times in the past. A change in the cell blank value enables a user to confirm an advantageous effect of the soaking and washing.

In a case where an operator determines that the cell blank value displayed on the cell blank value display area 903 is changed to a certain level or greater, the operator checks an additional washing setting check box 902a disposed for each reaction container in the washing state display area 902. In this manner, the soaking and washing can be additionally performed on only a specified reaction container. That is, the soaking and washing are performed on the reaction container 104 in which the additional washing setting check box 902a is checked, prior to the analysis in the reaction container during the analysis. The check box 902a may not be provided. A configuration may be adopted in which the reaction container is automatically selected as the soaking and washing target in a case where deviation in a certain level or greater is present between the predetermined reference value of the cell blank value and the cell blank value measured this time.

An advantageous effect of the present embodiment configured as described above will be described.

In facilities in which the automatic analysis device is always operated for 24 hours in preparation for urgent sample arrival, even if the soaking and washing are performed during standby as in the related art, in a case where an urgent sample analysis is needed, the soaking and washing have to be stopped, and there is no guarantee that a time for soaking can be sufficiently secured. In addition, if an operator tries to forcibly complete the soaking and washing, it is considered that the analysis process is hindered, thereby causing a possibility of degraded analysis efficiency.

In contrast, the present embodiment adopts the following configuration. After the analysis start instruction is input in a state where the sample is not dispensed to all of reaction containers mounted on the reaction disc, before completing the analysis preparation washing process for washing the reaction container to be used in analyzing the sample to be first analyzed, the soaking and washing process for performing soaking and washing during a predetermined period of time is controlled to be started by dispensing the soaking and washing detergent to another reaction container different from the reaction container. Therefore, the soaking and washing can be efficiently performed on the reaction container without hindering the analysis process.

REFERENCE SIGNS LIST

101 REAGENT DISC
102 REAGENT DISPENSING MECHANISM
103 SAMPLE DISPENSING MECHANISM
104 REACTION CONTAINER

105 REACTION DISC
106 REAGENT CONTAINER CONVEYANCE PATH
107 A/D CONVERTER
108 SAMPLE DISPENSING POSITION
109 THERMOSTATIC TANK
110 REAGENT CONTAINER
111 MIXING MECHANISM
112 CONTROL DEVICE
114 DISPLAY INPUT UNIT
115 SAMPLE CONTAINER RACK
116 SAMPLE CONTAINER CONVEYANCE PATH
117 SAMPLE CONTAINER
118 STORAGE DEVICE
119 WASHING MECHANISM
301 REACTION LIQUID SUCTION POSITION
302 DETERGENT 1 DISCHARGE POSITION
303 WATER DISCHARGE POSITION
304 CELL BLANK DISCHARGE POSITION
305 REMAINING WATER SUCTION POSITION
306 SAMPLE DISCHARGE POSITION
307 REAGENT DISCHARGE POSITION
701 REACTION SYSTEM WASHING SETTING SCREEN
702 WASHING INTERVAL INPUT AREA
703, 704 WASHING INTERVAL INPUT AREA
705, 706 WASHING NUMBER INPUT AREA
707, 805 OK BUTTON
708, 806 CANCELLATION BUTTON
801 WASHING SETTING SCREEN
802 BLOCK AREA
803 CONTAINER NUMBER INPUT AREA
804 DAY-OF-WEEK INPUT AREA
901 WASHING STATE DISPLAY SCREEN
902 WASHING STATE DISPLAY AREA
903 CELL BLANK VALUE DISPLAY AREA
904 WASHING STATE DISPLAY AREA
905 WASHING STATE DISPLAY AREA

The invention claimed is:

1. An automatic analysis device comprising:
a sample container conveyance path that conveys a plurality of sample containers respectively containing samples to be analyzed;
a reagent disc holding a plurality of reagent containers respectively containing reagents for use in analyzing the samples;
a reaction disk holding a plurality of reaction containers at respective positions around a circumference of the reaction disk;
a sample dispensing mechanism disposed at a sample dispensing position that is configured to dispense samples into reaction containers on the reaction disk and dispense a first detergent into reaction containers on the disk;
a photometer disposed at a photometer position that is configured to detect a light absorbance of a liquid within a reaction container on the reaction disk; and
a control device, connected to the reaction disk, the sample dispensing mechanism, and the photometer, that is programmed to:
upon receiving a start instruction to start analysis of at least a first sample contained in a first sample container of the plurality of sample containers, rotate the reaction disk so that a first reaction container at a first position of the reaction disk is positioned at each of a liquid suction position, a detergent discharge position, a water discharge position, and a remaining liquid position, in the afore-mentioned order, wherein each of the liquid suction position, the detergent discharge position, the water discharge position, and the remaining liquid positions are adjacent to the circumference of the reaction disk,
after rotating the first reaction container at the first position on the reaction disk to the remaining liquid position, rotate the first reaction container at the first position to the sample dispensing position and control the sample dispensing mechanism to discharge the first sample,
before controlling the sample dispensing mechanism to discharge the first sample and simultaneously while rotating the first reaction container at the first position on the reaction disk to each of the liquid suction position, the detergent discharge position, the water discharge position, and the remaining liquid position, control the sample dispensing mechanism to discharge the first detergent to a plurality of other reaction containers other than the first reaction container that are disposed at respective positions on the reaction disk, as the reaction disk rotates,
after the first sample is dispensed into the first reaction container rotate the reaction disk to the photometer position and control the photometer to analyze the sample by detecting a light absorbance of a reaction liquid including the first sample.

2. The automatic analysis device according to claim 1, further comprising a reagent dispensing mechanism disposed at a reagent dispensing position that is configured to dispense reagents into reaction containers on the reaction disk and dispense the first detergent into reaction containers on the disk.

3. The automatic analysis device according to claim 1, wherein the control device is programmed to determine a plurality of reaction container groups respectively configured to include one or more of the reaction containers,
wherein a first group of the groups includes the first reaction container and a second group of the groups includes the plurality of other reaction containers.

4. The automatic analysis device according to claim 3, wherein control the reaction disk to stop rotation at each of the liquid suction position, the detergent discharge position, the water discharge position, and the remaining liquid position,
wherein the groups include a third group which, upon receiving a start instruction subsequent to the previous start instruction, does not include any reaction containers that had the first detergent discharged therein, and
wherein after receiving the subsequent analysis start instruction, the reaction disk is rotated so that a reaction container of the third group is rotated directly to the sample dispensing position without stopping.

5. The automatic analysis device according to claim 3, further comprising:
a display unit connected to the control device,
wherein the control device is programmed to:
display, on the display unit, a setting screen for setting a number of the reaction containers which have the second detergent dispensed therein by the sample dispensing mechanism every day of the week.

6. The automatic analysis device according to claim 1, further comprising:
a cleaning mechanism disposed adjacent to the reaction disk, wherein at the liquid suction position, liquid within the first reaction container is suction by the cleaning mechanism, wherein at the detergent discharge position, a second detergent is discharged into the first reaction container by the cleaning mechanism, wherein at the water discharge position, water is discharged into the first reaction container by the cleaning mechanism, and wherein at the remaining liquid position, liquid is suctioned from the first reaction container by the cleaning mechanism.

\* \* \* \* \*